United States Patent [19]

Hoff

[11] Patent Number: Plant 7,302

[45] Date of Patent: Aug. 21, 1990

[54] LILY PLANT NAMED ITALIA

[75] Inventor: Petrus M. M. Hoff, Hem, Netherlands

[73] Assignee: Hoffgaarde B.V., Netherlands

[21] Appl. No.: 350,251

[22] Filed: May 11, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new lily plant name Italia particularly characterized by its yellow and pink bicolored flowers, plant height of approximately 150 cm, upright flowers, and very strong stems and leaves.

1 Drawing Sheet

The present invention comprises a new and distinct cultivar of lily, botanically known as Lilium (Asiatic hybrid), and hereinafter referred to by the cultivar name Italia.

Italia is a product of a planned breeding program which had the objective of creating new lily cultivars having early flowering bright colors, numerous flowers on a small bulb size, and good retention in the vase. Certain of these objectives were met by the new cultivar.

Italia was originated by me from a hybridization made in a controlled breeding program in Hem, The Netherlands in 1980. The male and female parents are unknown seedlings.

Italia was discovered and selected by me as one flowering plant within the progeny of the stated cross in June 1982 in a controlled environment in Hem, The Netherlands.

I accomplished the first act of asexual reproduction of Italia by scaling bulbs of the initial selection in September 1982 in a controlled environment in Hem. Horticultural examination of selected units initiated in July 1983 has demonstrated that the combination of characteristics as herein disclosed for Italia are firmly fixed and are retained through successive generations of asexual reproduction.

Italia has not been observed under all possible environmental conditions. The phenotype may vary significantly with variations in environment such as temperature, light intensity, and day length. The following observations, measurements, and comparisons describe plants grown in Hem, The Netherlands under greenhouse conditions which approximate those generally used in commercial practice.

The following traits have been repeatedly observed and are determined to be basic characteristics of Italia which in combination distinguish this lily as a new and distinct cultivar.

1. The height of the plant is approximately 150 cm.
2. The flower diameter is approximately 16 cm.
3. The flowers have yellow and pink bicolored flowers.
4. Size 10–12 produces an average of 3–8 flowers.
5. Very strong stems and leaves.
6. Upright flowers.

The accompanying photographic drawing shows typical flower characteristics of Italia, with colors being as true as possible with illustrations of this type.

In the following description, color references are made to The Royal Horticultural Society Colour Chart (R.H.S.). The color values were determined at approximately 8:00 a.m. on Oct. 10, 1988 under cloudy conditions at Hem.

Origin: Seedling.

Name: Italia.

Parentage:

*Female parent.*—Unknown seedling.

*Male parent.*—Unknown seedling.

*Classification.*—Asian hybrid.

Ploidy: Diploid.

Plant:

1. *Plant height (on opening of the anthers of the first flower).*—Very tall (150 cm) with upright flowers.
2. *Stalk.*—Anthocyanin coloring — absent. Color: light green. Growth of hair: absent. Internode length: average, uniform. Cross section: rounded. Bulbils: present (on parts above soil). Color of the bulbils: black.
3. *Leaf.*—Arrangement: alternate. Position: spread out. Top angle of the base with the stalk: at right angles. Length: short. Width: medium. Thickness: normal. Form (middle third part of the stalk): elliptical. Color of the top side: light green, 137C. Luster of the top side: strong. Growth of hair at the bottom: absent. Apex: acute. Curve of the edge: lacking. Membraneous edge: lacking. Indentation of the edge: lacking. Uniformity of shape: present. Form in cross section: flat. Distal part: incurved. Flexibility: medium. Petiole: absent.

Flower:

1. *Structure.*—Type: umbellate. Secondary flowers: present. Growth of hair: absent. Bracts: absent. Bracteole: absent. Position: erect. Type: bowl-shaped. Diameter: medium. Height of crown: medium. Length of longest pedical: medium.
2. *Petal.*—Length of longest outer petal: long. Width of widest outer petal: medium. Length of longest interior petal: long. Width of widest interior petal: medium. Color of the inside of the interior petal: 10A. Color of the outside of the interior petal: 37A. Color of the inside of the outer petal: 10A. Color of the outside of the outer petal: 37A. Marking on the inside: present. Color of the marking: 166A. Type of marking on the inside: spots. Density of the spots in the marking: medium. Color of the inner side of the throat: 10A. Color of the outer side of the throat: 10A. Texture of the inside: papillose. Luster of the inside: lacking. Curve of the edges of the petal: absent. Curvature of petals: present. Bended part of the petals: entire petal. Extent of bending: medium. Fragrance: lacking.

Reproductive organs:

*Length of stamens.*—Short.

*Color of the filaments.*—White.

*Color of the anthers.*—Brown.

*Color of pollen.*—Pale brown.

*Length of the pistil.*—Long.

*Color of the style.*—Green.

*Color of the stigma.*—Brown.

Bulb:

*Type (in dormant season).*—Type 4.

*Apex.*—Pointed.

*Density of scales.*—Dense.

*Color of the exterior scales.*—White.

*Apex of the scales.*—Pointed.

*Underground part of the stalk.*—Bulblets — present. Roots — present.

I claim:

1. A new and distinct cultivar of lily plant named Italia, as illustrated and described.

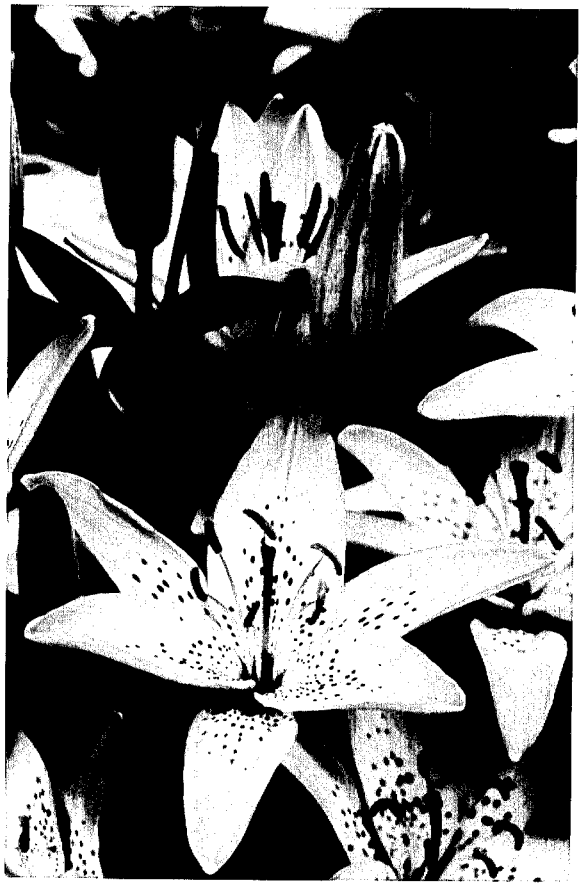

* * * * *